United States Patent [19]

Gerhold

[11] 4,402,832
[45] Sep. 6, 1983

[54] HIGH EFFICIENCY CONTINUOUS SEPARATION PROCESS

[75] Inventor: Clarence G. Gerhold, Palatine, Ill.

[73] Assignee: UOP Inc., Des Plaines, Ill.

[21] Appl. No.: 407,680

[22] Filed: Aug. 12, 1982

[51] Int. Cl.³ ............................................. B01A 15/03
[52] U.S. Cl. ........................................ 210/659; 55/67; 127/46.2
[58] Field of Search ...................... 210/696, 659; 55/67, 55/197; 127/46.2

[56] References Cited

U.S. PATENT DOCUMENTS

| | | | |
|---|---|---|---|
| 2,985,589 | 5/1961 | Broughton | 210/34 |
| 3,040,777 | 6/1962 | Carson et al. | 137/625.15 |
| 3,205,166 | 9/1965 | Ludlow et al. | 208/310 |
| 3,291,726 | 12/1966 | Broughton | 208/310 |
| 3,310,486 | 3/1967 | Broughton et al. | 208/310 |
| 3,416,961 | 12/1968 | Mountfort | 127/46 |
| 3,422,848 | 1/1969 | Liebman et al. | 137/625.15 |
| 3,455,815 | 7/1969 | Fickel | 208/310 |
| 3,458,437 | 7/1969 | Ouano | 210/659 |
| 3,686,117 | 8/1972 | Lauer et al. | 210/31 C |
| 3,715,409 | 2/1973 | Broughton | 260/674 SA |
| 4,001,112 | 1/1977 | Barker | 210/659 |
| 4,022,637 | 5/1977 | Sutthoff et al. | 127/46 A |
| 4,031,155 | 6/1977 | Healy et al. | 260/674 A |
| 4,155,846 | 6/1979 | Novak et al. | 210/31 C |
| 4,157,267 | 6/1979 | Odawara et al. | 127/46 A |
| 4,267,054 | 5/1981 | Yoritomi et al. | 210/659 |
| 4,332,623 | 1/1982 | Ando et al. | 127/46.2 |
| 4,366,060 | 12/1982 | Leiser et al. | 210/659 |

FOREIGN PATENT DOCUMENTS 55-118400 9/1980 Japan.

*Primary Examiner*—John Adee
*Attorney, Agent, or Firm*—James R. Hoatson, Jr.; Louis A. Morris; William H. Page, II

[57] ABSTRACT

A process for separating an extract component from a raffinate component contained in a feed mixture. A unidirectional fluid flow system is maintained through a series of separating units through which the components travel at different rates. A component concentration distribution is established within the system of units and divided into specific zones. Feed and displacement fluid are passed into the inlets of two of the units and extract and raffinate are taken as the entire streams from outlets of two of the units all at appropriate points on the component concentration distribution. Other inlets and outlets of the various units lying in the same zone are interconnected. At the appropriate times the inlets and outlets are shifted so as to simulate movement of the units in a direction co-current with the fluid flow and thereby enable the inlets and outlets to continually lie in the appropriate zones.

11 Claims, 18 Drawing Figures

HIGH EFFICIENCY CONTINUOUS SEPARATION PROCESS

BACKGROUND OF THE INVENTION

1. Field of the Invention

The field of art to which this invention pertains is the separation of a component from a fluid mixture of components.

2. Description of the Prior Art

There are many separation processes known for separating components from a fluid mixture. Fractional distillation or crystallization are examples of means ideal for separating liquid mixtures of components having different boiling points or freezing points, respectively. Gas or liquid chromatography makes use of material or adsorbents having varying degrees of affinity for different components of a fluid mixture, thereby causing the components to separate as they flow through the material. Similarly, materials known as molecular sieves may affect the rates at which each component of a fluid mixture passes through them by admitting only molecules of certain of the components into the pore structure of the material, but not other components, thus the component for which the material in question has the greater affinity or retention capacity may be recovered or "desorbed" by means of a desorbent material.

A very successful process for separating components from a feed mixture based on the use of adsorbents or molecular sieves for chromatographic type separations is the countercurrent moving-bed or simulated moving-bed countercurrent flow system. In the moving-bed or simulated moving-bed processes the adsorption and desorption operations are continuously taking place which allows both continuous production of an extract (more selectively adsorbed component) and a raffinate (less selectively adsorbed component) stream and the continual use of feed and desorbent streams. The operating principles and sequence of such a flow system are described in U.S. Pat. No. 2,985,589 to Broughton et al. In that system it is the progressive movement of multiple liquid access points down an adsorbent chamber that simulates the upward movement of adsorbent contained in the chamber. Only four of the access lines are active at any one time: the feed input stream, desorbent inlet stream, raffinate outlet stream, and extract outlet stream access lines. Coincident with this simulated upward movement of the solid adsorbent is the movement of the liquid occupying the void volume of the packed bed of adsorbent. So that countercurrent contact is maintained, a liquid flow down the adsorbent chamber may be provided by a pump. As an active liquid access point moves through a cycle, that is, from the top of the chamber to the bottom, the chamber circulation pump moves through different zones which require different flow rates. A programmed flow controller may be provided to set and regulate these flow rates.

The active liquid access points effectively divide the adsorbent chamber into separate zones, each of which has a different function. It is generally necessary that three separate operational zones be present in order for the process to take place although in some instances an optional fourth zone may be used.

The adsorption zone, zone 1, is defined as the adsorbent located between the feed inlet stream and the raffinate outlet stream. In this zone, the feed stock contacts the adsorbent, an extract component is adsorbed, and a raffinate stream is withdrawn. Since the general flow through zone 1 is from the feed stream which passes into the zone to the raffinate stream which passes out of the zone, the flow in this zone is considered to be a downstream direction when proceeding from the feed inlet to the raffinate outlet streams.

Immediately upstream with respect to fluid flow in zone 1 is the purification zone, zone 2. The purification zone is defined as the adsorbent between the extract outlet stream and the feed inlet stream. The basic operations taking place in zone 2 are the displacement from the non-selective void volume of the adsorbent of any raffinate material carried into zone 2 by the shifting of adsorbent into this zone and the desorption of any raffinate material adsorbed within the selective pore volume of the adsorbent or adsorbed on the surfaces of the adsorbent particles. Purification is achieved by passing a portion of extract stream material leaving zone 3 into zone 2 at zone 2's upstream boundary, the extract outlet stream, to effect the displacement of raffinate material. The flow of material in zone 2 is in a downstream direction from the extract outlet stream to the feed inlet stream.

Immediately upstream of zone 2 with respect to the fluid flowing in zone 2 is the desorption zone or zone 3. The desorption zone is defined as the adsorbent between the desorbent inlet and the extract outlet stream. The function of the desorption zone is to allow a desorbent material which passes into this zone to displace the extract component which was adsorbed upon the adsorbent during a previous contact with feed in zone 1 in a prior cycle of operation. The flow of fluid in zone 3 is essentially in the same direction as that of zones 1 and 2.

In some instances an optional buffer zone, zone 4, is utilized. This zone, defined as the adsorbent between the raffinate outlet stream and the desorbent inlet stream, if used, is located immediately upstream with respect to the fluid flow to zone 3. Zone 4 would be utilized to conserve the amount of desorbent utilized in the desorption step since a portion of the raffinate stream which is removed from zone 1 can be passed into zone 4 to displace desorbent material present in that zone out of that zone into the desorption zone. Zone 4 will contain enough adsorbent so that raffinate material present in the raffinate stream passing out of zone 1 and into zone 4 can be prevented from passing into zone 3 thereby contaminating extract stream removed from zone 3. In the instances in which the fourth operational zone is not utilized the raffinate stream passed from zone 1 to zone 4 must be carefully monitored in order that the flow directly from zone 1 to zone 3 can be stopped when there is an appreciable quantity of raffinate material present in the raffinate stream passing from zone 1 into zone 3 so that the extract outlet stream is not contaminated.

A cyclic advancement of the input and output streams through the fixed bed of adsorbent can be accomplished by utilizing a manifold system in which the valves in the manifold are operated in a sequential manner to effect the shifting of the input and output streams thereby allowing a flow of fluid with respect to solid adsorbent in a countercurrent manner. Another mode of operation which can effect the countercurrent flow of solid adsorbent with respect to fluid involves the use of a rotating disc valve in which the input and output streams are connected to the valve and the lines through which feed input, extract output, desorbent input and raffinate output streams pass are advanced in the same direction through the adsorbent bed. Both the manifold arrangement and disc valve are known in the art. Specifically rotary disc valves which can be utilized in this prior art operation can be found in U.S. Pat. Nos. 3,040,777 to Carson et al and 3,422,848 to Liebman et al. Both of the aforementioned patents disclose a rotary type connection valve in which the suitable advancement of the various input and output streams from fixed sources can be achieved without difficulty.

In many instances, one operational zone will contain a much larger quantity of adsorbent than some other operational zone. For instance, in some operations the buffer zone can contain a minor amount of adsorbent as compared to the adsorbent required for the adsorption and purification zones. It can also be seen that in instances in which desorbent is used which can easily desorb extract material from the adsorbent that a relatively small amount of adsorbent will be needed in a desorption zone as compared to the adsorbent needed in the buffer zone or adsorption zone or purification zone or all of them. Since it is not required that the adsorbent be located in a single column, the use of multiple chambers or a series of columns is within the scope of the process.

It is not necessary that all of the input or output streams be simultaneously used, and in fact, in many instances some of the streams can be shut off while others effect an input or output of material. The apparatus which can be utilized to effect this prior art process can also contain a series of individual beds connected by connecting conduits upon which are placed input or output taps to which the various input or output streams can be attached and alternately and periodically shifted to effect continuous operation. In some instances, the connecting conduits can be connected to transfer taps which during the normal operations do not function as a conduit through which material passes into or out of the process.

It is usually essential to the prior art simulated moving-bed process that at least a portion of the extract output stream will pass into a separation means wherein at least a portion of the desorbent material can be separated to produce an extract product containing a reduced concentration of desorbent material. Preferably at least a portion of the raffinate output stream will also be passed to a separation means wherein at least a portion of the desorbent material can be separated to produce a desorbent stream which can be reused in the process and a raffinate product containing a reduced concentration of desorbent material. The separation means will typically be a fractionation column, the design and operation of which is well known to the separation art.

Further reference can be made to D. B. Broughton U.S. Pat. No. 2,985,589, and to a paper entitled "Continuous Adsorptive Processing—A New Separation Technique" by D. B. Broughton presented at the 34th Annual meeting of the Society of Chemical Engineers at Tokyo, Japan on April 2, 1969, for further explanation of the simulated moving-bed counter-current process flow scheme.

There have been other flow schemes since the above basic Broughton et al invention which are also based in some manner or chromatographic separation of feed stream components through the establishment of a concentration gradient of such components in a bed or beds of adsorbent material exhibiting adsorptive selectivity for one component over another. For example, Japanese Public Disclosure 118400/80 (Public Disclosure Date Sept. 11, 1980) of Miyahara et al discloses the use of a single (non-simulated moving-bed) column of ion exchange resin with an inlet at the top and an outlet at the bottom for the separation of glucose from fructose by sequentially passing into the column, in the appropriate order, the feed stream, the desorbent stream and various effluent streams held in intermediate storage, each stream being introduced at the appropriate time with relation to the concentration gradient in the column. Similarily, in the process of U.S. Pat. No. 4,267,054 to Yoritomi et al a concentration gradient is established in one or more columns (simulated moving-bed) with the discontinuous and intermittent introduction of the feed and desorbent streams which cause disturbance of the gradient and the introduction of various recycle streams direct from the column effluent (rather than intermediate storage) as appropriate to re-establish the concentration gradient. Other examples of processes involving flow schemes similar to any of the above art, but no more relevant to the present invention, are as set forth in U.S. Pat. Nos. 3,205,166 to Ludlow et al (actual moving bed); 3,291,726 to Broughton; 3,310,486 to Broughton et al; 3,416,961 to Mountfort et al; 3,455,815 to Fickel; 3,686,117 to Lauer et al; 3,715,409 to Broughton; 4,155,846 to Novak et al; 4,157,267 to Odawara et al; 4,022,637 to Sutthoff et al; 4,031,155 to Healy et al; and 4,332,623 to Ando et al.

In contradistinction to the above discussed prior art, the present invention achieves chromatographic separation of components of a feed mixture by the employment of a simulated moving-bed co-current flow system without, inter alia, the purification or buffering zones such as in Broughton et al (U.S. Pat. No. 2,985,589), the intermediate storage such as in Miyahara et al or the discontinuous and intermittent characteristics such as in Yoritomi et al.

SUMMARY OF THE INVENTION

The present invention in its broadest embodiment comprises a process for separating an extract component from a raffinate component contained in a feed mixture comprising the steps of: (a) maintaining a unidirectional fluid flow system through a series of separating units in which the components have differential rates of travel due to selective retention or acceleration of the components in each of the units, each of the units having a fluid inlet and a fluid outlet; (b) passing the feed mixture into one of the fluid inlets and a displacement fluid into another of the fluid inlets, the displacement fluid being capable of displacing the components from the separating units; (c) establishing within a system comprising the fluid flow system a component concentration distribution, zones of which comprise, sequentially, the highest purity displacement fluid (zone I), extract component diluted with displacement fluid (zone II), concentrated extract component (zone III), extract and raffinate component mixture with the extract component being the major component (zone IV), extract and raffinate component mixture with the raffinate component being the major component (zone V), concentrated raffinate component (zone VI), and raffinate component diluted with displacement fluid (zone VII), each of the zones II, IV, V and VII having associated with it one of the fluid inlets and one of the fluid outlets, zone I having the fluid inlet for displacement fluid associated with it and each of zones III and VI having associated with it a fluid outlet, the feed mixture being passed through a fluid inlet the locus of which is at least proximate to the point on the component concentration distribution where the relative proportions of the extract and raffinate components are the same as that occurring in the feed mixture; (d) withdrawing an extract stream comprising the entire flow from the fluid outlet of zone III, and withdrawing a raffinate stream comprising the entire flow from the fluid outlet of zone VI; (e) passing the entire stream from each of the fluid outlets of the zones II, IV, V and VII to a corresponding fluid inlet, the locuses of each outlet and corresponding inlet being within the same zone of the component concentration distribution; and (f) periodically simultaneously effecting the following shifting of the inlets and outlets: the feed mixture fluid inlet to what prior to the shift was the inlet of zone V, the inlet zone V to what had been the inlet of zone VII, the inlet of zone VII to what had been the inlet of zone I, the inlet of zone I to what had been the inlet of zone II, the inlet of zone II to what had been the inlet of zone IV, the inlet of zone IV to what had been the feed mixture inlet, the outlet of zone II to what had been the outlet of zone III, the outlet of zone III to what had been the outlet of zone IV, the outlet of zone IV to what had been the outlet of zone V, the outlet of zone V to what had been the outlet of zone VI, the outlet of zone VI to what had been the outlet of zone VII, and the outlet of zone VII to what had been the outlet of zone II, the shifting being effected prior to the progression through the units of the component concentration distribution to the extent that the composition of the inlet or outlet streams to or from any zone becomes inconsistent with the desired composition of that zone.

Other embodiments of the invention relates to flow rates, conditions and process details as well as the specific configurations of the flow scheme of the present invention.

DETAILED DESCRIPTION OF THE INVENTION

Figure 1:
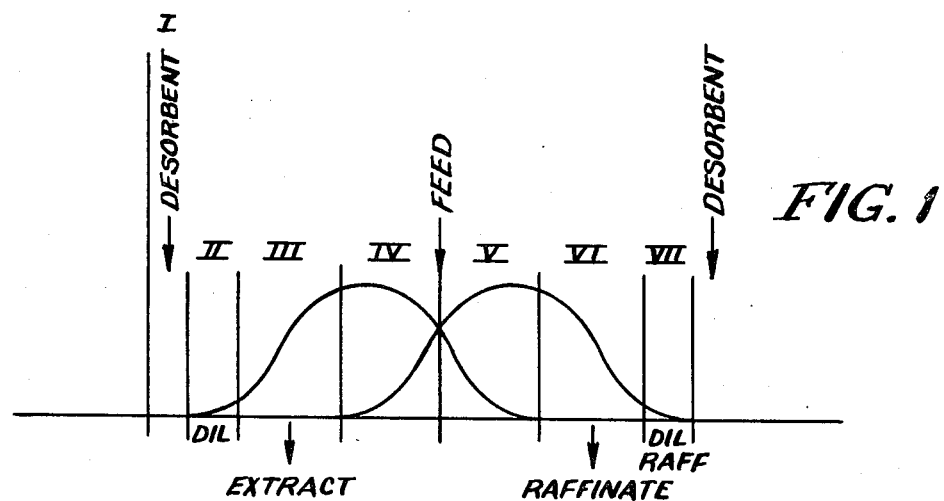
FIG. 1 is a plot of concentration gradients on which the present invention is based.

At the onset it is desirous to point out that it is contemplated that the present invention would be efficacious regardless of the separating means employed. The only general limitations are that the flow streams are fluid and that in fact a separation is accomplished by the separating unit in question. Thus, the separating units might comprise, for example, units in which the selected component acceleration or retardation results from partial vaporization, selective dialysis, electrophoresis, selective diffusion, or passage through beds of molecular sieves or other selective adsorbents. For the sake of convenience, it is the last mentioned separation means that will be emphasized for purposes of the following discussion, although it should be understood that the present invention is not limited to the use of such means and that the various components of the adsorptive separation means has functional parallels in other means. Contact of the feed mixture with the adsorbent will occur at adsorption conditions and contact with the desorbent at desorption conditions, all such conditions preferably comprising temperatures and pressures which effect liquid phase.

The definitions of various terms used throughout the specification will be useful. A "feed mixture" is a mixture containing one or more extract components and one or more raffinate components to be separated by my process. The term "feed stream" indicates a stream of a feed mixture which passes to the adsorbent used in the process. An "extract component" is a component which, because it is adsorbed, moves more slowly through the system, while a "raffinate component" is a component which because it is less selectively adsorbed, moves more rapidly through the system. The term "desorbent material" shall means generally a displacement fluid capable of desorbing and displacing both the extract and raffinate components, but at different rates. The term "desorbent stream" or "desorbent input stream" indicates the stream through which desorbent material passes to the system. The term "raffinate stream" or "raffinate output stream" means a stream through which a raffinate component is removed from the system. The term "extract stream" or "extract output stream" shall mean a stream through which an extract material which has been desorbed by a desorbent material is removed from the system. Practically speaking, the extract and raffinate output streams will be diluted to some extent by the desorbent material, although significantly less than the dilution which occurs in the process of the above U.S. Pat. No. 2,985,589 to Broughton, et al. Final separation, therefore, usually requires steps for removal and recovery of the desorbent material for each of the separated product streams.

The term "selective pore volume" of the adsorbent is defined as the volume of the adsorbent which selectively adsorbs an extract component from the feed mixture. The term "non-selective void volume" of the adsorbent is the volume of the adsorbent which does not selectively retain an extract component from the feed mixture. This volume includes the cavities of the adsorbent which contain no adsorptive sites and the interstitial void spaces between adsorbent particles. The selective pore volume and the non-selective void volume are generally expressed in volumetric quantities and are of importance in determining the proper flow rates of fluid required to be passed into a zone for efficient operations to take place for a given quantity of adsorbent. When adsorbent "passes" into a zone (hereinafter defined and described), its non-selective void volume, together with its selective pore volume, carries fluid into that zone. The selective pore volume of an adsorbent can in certain instances adsorb portions of raffinate material from the fluid surrounding the adsorbent, since in certain instances there is competition betweeen extract material and raffinate material for adsorptive sites within the selective pore volume. If a large quantity of raffinate material with respect to extract material surrounds the adsorbent, raffinate material can be competitive enough to be adsorbed by the adsorbent.

Desorbent materials used in various prior art adsorptive separation processes vary depending upon such factors as the type of operation employed. In the swing-bed system, in which the selectively adsorbed feed component is removed from the adsorbent by a purge stream, desorbent selection is not as critical and desorbent material comprising gaseous hydrocarbons such as methane, ethane, etc., or other types of gases such as nitrogen or hydrogen, may be used at elevated temperatures or reduced pressures or both to effectively purge the adsorbed feed component from the adsorbent, if the adsorbed feed component is volatile. However, in adsorptive separation processes which are generally operated continuously at substantially constant pressures and temperatures to ensure liquid phase, the desorbent material must be judiciously selected to satisfy many criteria. First, the desorbent material should displace an extract component from the adsorbent with reasonable mass flow rates without itself being so strongly adsorbed as to unduly prevent an extract component from displacing the desorbent material in a following adsorption cycle. Expressed in terms of the selectivity (hereinafter discussed in more detail), it is preferred that the adsorbent be more selective for all of the extract components with respect to a raffinate component than it is for the desorbent material with respect to a raffinate component. Secondly, desorbent materials must be compatible with the particular adsorbent and the particular feed mixture. More specifically, they must not reduce or destroy the critical selectivity of the adsorbent for an extract component with respect to a raffinate component. Additionally, desorbent materials should not chemically react with or cause a chemical reaction of either an extract component or a raffinate component. Both the extract stream and the reffinate stream are typically removed from the adsorbent in admixture with desorbent material and any chemical reaction involving a desorbent material and an extract component or a raffinate component would reduce the purity of the extract product or the raffinate product or both. Since both the raffinate stream and the extract stream typically contain desorbent materials, desorbent materials should additionally be substances which are easily separable from the feed mixture that is passed into the process. Without a method of separating at least a portion of the desorbent material present in the extract stream and the raffinate stream, the concentration of an extract component in the extract product and the concentration of a raffinate component in the raffinate product might not be as high as desired, nor would the desorbent material be available for resuse in the process. It is contemplated that at least a portion of the desorbent material might be separated from the extract and the raffinate streams by distillation or evaporation, but other separation methods such as reverse osmosis may also be employed alone or in combination with distillation or evaporation. If the raffinate and extract products are foodstuffs intended for human consumption, desorbent materials should also be non-toxic. Finally, desorbent materials should also be materials which are readily available and therefore reasonable in cost.

The prior art has recognized that certain characteristics of adsorbents are high desirable, if not absolutely necessary, to the successful operation of a selective adsorption process. Such characteristics are equally important to the embodiment of this process illustrated. Among such characteristics are: adsorptive capacity for some volume of an extract component per volume of adsorbent; the selective adsorption of an extract component with respect to a raffinate component and the desorbent material; and sufficiently fast rates of adsorption and desorption of an extract component to and from the adsorbent. Capacity of the adsorbent for adsorbing a specific volume of an extract component is, of course, a necessity; without such capacity the adsorbent is useless for adsorptive separation. Furthermore, the higher the adsorbent's capacity for an extract component, the better is the adsorbent. Increased capacity of a particular adsorbent makes it possible to reduce the amount of adsorbent needed to separate an extract component of known concentration contained in a particular charge rate of feed mixture. A reduction in the amount of adsorbent required for a specific adsorptive separation reduces the cost of the separation process. It is important that the good initial capacity of the adsorbent be maintained during actual use in the separation process over some economically desirable life. The second necessary adsorbent characteristic is the ability of the adsorbent to separate components of the feed; or, in other words, that the adsorbent possess adsorptive selectivity, (B), for one component as compared to another component. Relative selectivity can be expressed not only for one feed component as compared to another but can also be expressed between any feed mixture component and the desorbent material. The selectivity, (B), as used throughout this specification is defined as the ratio of the two components of the adsorbed phase over the ratio of the same two components in the unadsorbed phase at equilibrium conditions. Relative selectivity is shown as Equation 1 below:

Equation 1
$$\text{Selectivity} = (B) = \frac{[\text{vol. percent } C/\text{vol. percent } D]_A}{[\text{vol. percent } C/\text{vol. percent } D]_U}$$

where C and D are two components of the feed represented in volume percent and the subscripts A and U represent the adsorbed and unadsorbed phases respectively. The equilibrium conditions are determined when the feed passing over a bed of adsorbent did not change composition after contacting the bed of adsorbent. In other words, there is no net transfer of material occurring between the unadsorbed and adsorbed phases. Where selectivity of two components approaches 1.0, there is no preferential adsorption of one component by the adsorbent with respect to the other; they are both adsorbed (or non-adsorbed) to about the same degree with respect to each other. As the (B) becomes less than or greater than 1.0, there is a preferential adsorption by the adsorbent for one component with respect to the other. When comparing the selectivity by the adsorbent of one component C over component D, a (B) larger than 1.0 indicates preferential adsorption of component C within the adsorbent. A (B) less than 1.0 would indicate that component D is preferentially adsorbed leaving an unadsorbed phase richer in component C and an adsorbed phase richer in component D. Ideally, desorbent materials should have a selectivity equal to about 1 or slightly less than 1 with respect to all extract components so that all of the extract components can be desorbed as a class with reasonable flow rates of desorbent material and so that extract components can displace desorbent material in a subsequent adsorption step. While separation of an extract component from a raffinate component is theoretically possible when the selectivity of the adsorbent for the extract component with respect to the raffinate component is greater than 1.0, it is preferred that such selectivity be greater than 2.0. Like relative volatility, the higher the selectivity the easier the separation is to perform. Higher selectivities permit a smaller amount of adsorbent to be used. The third important characteristic is the rate of exchange of the extract component of the feed mixture material or, in other words, the relative rate of desorption of the extract component. This characteristic relates directly to the amount of desorbent material that must be employed in the process to recover the extract component from the adsorbent; faster rates of exchange reduce the amount of desorbent material needed to remove the extract component and therefore permit a reduction in the operating cost of the process. With faster rates of exchange, less desorbent material has to be pumped through the process and separated from the extract stream for reuse in the process.

With the above background information, attention may now be directed specifically to the present invention. With reference to FIG. 1, there is shown a plot of two overlapping curves, one, as indicated, being the concentration gradient of a relatively retained component through the system (hereinafter defined) and the second, as indicated, being the corresponding concentration gradient for the relatively non-retained or acceleration component. The retention or acceleration results, depending on the separation means in question, from the selective adsorption, volatility, diffusion or reaction to externally applied fields of the various components. The ordinate of the plot represents the magnitude of the concentration of a component at a point in question on the curve while the abscissa represents the position of that point in the system at a specific instant. The plot of FIG. 1 may be deemed indicative of the appearance of what the concentration gradients in a solid bed adsorptive system of a more selectively adsorbed component (component 1) and a less selectively adsorbed component (component 2) throughout a packed bed would be a given time after a slug of feed comprising a mixture of the components is introduced into the bed followed by a continuous flow of displacement fluid (desorbent) which is capable of effecting desorption of component 1 from the adsorbent. Components 1 and 2 separate at least partially because of the selective retention of component 1 resulting from the selective adsorption of component 1.

The above plot, as shown in FIG. 1, for purposes of the present invention, is divided into seven specific zones, as indicated. The first zone (zone I) is that of pure (or the highest purity) displacement fluid (desorbent) which is the location in the system at which desorbent is introduced. The second zone (zone II) is that of extract component (component 1) diluted with desorbent. The third zone (zone III) is that of concentrated extract component. The fourth zone (zone IV) is that of impure extract or extract and raffinate component (component 2) mixture with the extract component being the major component. The fifth zone (zone V) is that of impure raffinate or extract and raffinate component mixture with the raffinate component being the major component. The sixth zone (zone VI) is that of concentrated raffinate component. The seventh zone (zone VII) is that of raffinate component diluted with desorbent.

The essence of the present invention lies in a unique process based on the plot of FIG. 1 which establishes the zones of FIG. 1 as a dynamic system in a series of separating units. In arriving at the present invention, the inventor imagined the inlet stream to each zone and the feed stream inlet to be analogous to the inlet streams of a series of separating units with the inlet streams of the units arranged in the same order as the inlets to the zones of FIG. 1. Thus, beginning arbitrarily with the feedstream as the inlet stream to a first separating unit (the separating units being numbered sequentially from left to right) and looking from right to left on the plot of FIG. 1, the inlet stream to the next or second separating unit would be that of zone IV, the inlet stream to a third separating unit would be that of zone II (zone III is for concentrated extract, a product stream, and as such has no inlet stream associated with it), the inlet stream to a fourth separating unit would be that of zone I, the inlet stream to a fifth separating unit would be that of zone VII (continuing at the opposite end of the plot, and again from right to left), and the inlet stream to a sixth separating unit would be that of zone V (zone VI is for concentrated raffinate, a product stream, and as such has no inlet stream associated with it).

Similarly, the outlet streams of the units are arranged in the same order as the outlets to the zones of FIG. 1. Thus, beginning arbitrarily with the zone IV outlet stream as the outlet stream to the first separating unit and looking from right to left on the plot of FIG. 1, the outlet stream to the second separating unit would be that of zone III (extract product), the outlet stream to the third separating unit would be that of zone II, the outlet stream to the fourth separating unit would be that of zone VII (zone I is the desorbent inlet, strictly an inlet stream, and as such has no outlet stream associated with it), the outlet stream to the fifth separating unit would be that of zone VI, and the outlet stream to the sixth separating unit would be that of zone V.

Figure 2:
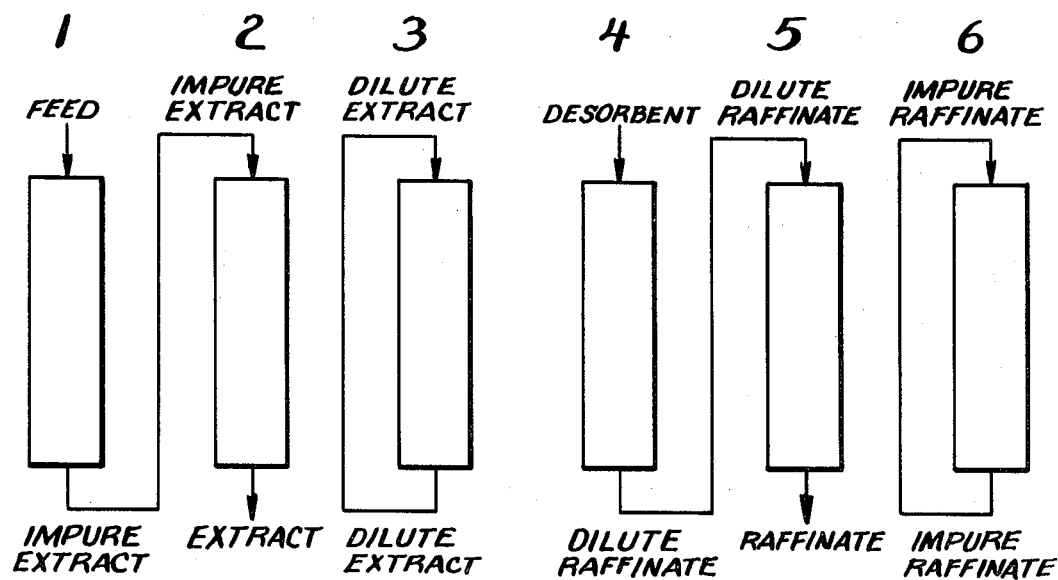
FIG. 2 is a flow diagram of the separating units of the present invention showing the various inlet and outlet streams and the location relationships of those streams for a particularly preferred embodiment of the invention.

We look now to FIG. 2 for a schematic representation of the above six separating units (the units being numbered sequentially from left to right in accordance with the above discussion) and the associated inlet and outlet streams as established above. The sequence of the inlet streams and sequence of the outlet streams as shown are each fixed in accordance with the plot of FIG. 1 and will not vary. What may vary is the correspondence between the inlets and outlets of the separating units, since as stated above, the starting point in going through the sequence of inlet and outlet streams is arbitrary, e.g., if in the above discussion the outlet of zone III (concentrated extract) was specified as the outlet of the first separating unit, then each outlet as shown in FIG. 2 would be shifted one to the left with the zone IV outlet becoming the outlet of the sixth separating unit. There are, therefore, six possible embodiments of the present invention, one of which is as shown in FIG. 2.

Another essential feature of the present invention is that inlets and outlets lying in the same zone are connected, as is also shown in FIG. 2, e.g. the outlet of the first separating unit is connected to the inlet of the second because that particular inlet and outlet both lie in zone IV. It should be noted with regard to the embodiment of the present invention shown in FIG. 2 that zones II and V lie in their entirety in the third and sixth separating units, respectively. The inlets and outlets of each of these two units are therefore connected to each other and the flow that occurs in both instances from these outlets to inlets is referred to as "pumparound." For reasons hereinafter discussed, those two embodiments of the invention having two separating units where pumparound occurs are the preferred embodiments.

Flow of fluids through the separating units, as indicated in FIG. 2, is continuous and unidirectional. In the course of such flow, the concentration gradient of FIG. 1 which occurs in the actual system is by no means static, but tends to progress as a wave (moving to the right) through the system and, therefore, the zones progress in a like manner. The various inlet and outlet streams would, thus, soon not be associated with the appropriate zones if some compensating means were not employed. The means employed are similar to those disclosed for the simulated moving bed in the above discussed U.S. Pat. No. 2,985,589 to Broughton et al, i.e. the inlets and outlets are periodically simultaneously shifted to keep pace with the progression of the curves. However unlike the simulated moving bed countercurrent flow systems of Broughton et al, the effect of the shifting in the present invention is a co-current movement of the beds with the fluid flow. The shifting effected is: the feed mixture inlet to what prior to the shift was the inlet of zone V, the inlet of zone V to what had been the inlet of zone VII, the inlet of zone VII to what had been the inlet of zone I, the inlet of zone I to what had been the inlet of zone II, the inlet of zone II to what had been the inlet of zone IV, the inlet of zone IV to what had been the feed mixture inlet, the outlet of zone II to what had been the outlet of zone III, the outlet of zone III to what had been the outlet of zone IV, the outlet of zone IV to what had been the outlet of zone V, the outlet of zone V to what had been the outlet of zone VI, the outlet of zone VI to what had been the outlet of zone VII, and the outlet VII to what had been the outlet of zone II. The foregoing shifting should each time be carried out prior to the progression through the units of the component concentration distribution to the extent that the composition of the inlet or outlet streams to or from any zone becomes inconsistent with the desired composition of that zone.

With further reference to the Broughton et al patent, there are fundamental distinctions between the process of that patent and the present invention which should be emphasized. In the former process there is a constant recirculation of fluid through a continuous adsorbent bed in which the various zones lie, and the inlet and outlet streams, never constitute more than a portion of the flow through the bed at the point of their introduction or removal. It is necessary to establish composition interfaces in the bed to preclude, as a result of the simulated movement of the bed, the carrying of raffinate by the bed into the desorption zone and the carrying of extract into the adsorption zone. Thus, the purpose of the purification zone is to establish one such interface and flush raffinate component from a portion of the bed with fluid from the desorption zone prior to that portion comprising part of the desorption zone, and the purpose of the buffer zone is to establish the other interface and flush extract component from a portion of the bed with fluid from the adsorption zone prior to that portion comprising part of the adsorption zone. There is, therefore, in the prior art process a constant remixing of extract and raffinate components already separated to result in an inherent and unavoidable inefficiency in the process.

In the process of the present invention, the six discrete separating units, as compared to the continuous adsorbent bed of the prior art process, enable the individual bed fluid compositions to keep pace with the progression of the concentration gradients and there is no need to flush, purify or buffer a given bed prior to it shifting into a particular zone because that bed will already have acquired the appropriate composition. There can be no mixing of concentrated extract or raffinate with impure fluid compositions because the entire fluid flow in the zones of concentrated raffinate and extract are removed from the system as outlet streams from the separating units in those zones. Impure and dilute streams are retained in the system for further purification and concentration.

To achieve the purification and buffering required by the Broughton et al prior art process, a large amount of desorbent material must be injected into the system for recirculation through the zones. This desorbent material must ultimately be removed as a substantial diluent in the product streams from which in turn it must be removed such as by conventional distillation to obtain concentrated product. The product streams of the present invention will also be diluted with desorbent material, but to far less an extent, thus enabling a considerable savings in the energy required to recover the desorbent material from the product streams as compared to the prior art process.

There are other inherent advantages of the present invention as compared to processes of the prior art, particularly Broughton et al. The reduced rate of fluid circulation, particularly liquid, through the separating units required by the process of the present invention enables denser packing in the adsorbent system embodiments, due to proportionally less pressure drop at the lower rates, which in turn minimizes channeling through the adsorbent bed as well as minimizing void volume, the latter minimization being conductive to more rapid separation. The lack of intermediate inlet and outlet streams in the separating units of the present invention precludes the need for internal structures that would be required to accommodate such streams.

Optimum separation through use of the present invention depends on the coordination of the differential component movement rates through the separating units with the step or shift timing and the feed, withdrawal and inter-intra unit circulation rates. Thus, the flow rates of the fluid streams to the fluid inlets and from the fluid outlets are adjusted to provide the desired transition compositions of each inlet and outlet stream at the start and end of each flow period between each shift. Another control over those transition compositions is obtained in those embodiments of the present invention having the aforementioned pumparound which enable the composition distribution in each separate unit having a pumparound to be adjusted by varying the pumparound rate independently of the rest of the system. Conceivably, a given pumparound rate in these embodiments could become zero if the resulting less than ideal concentration gradients in the remaining zones could be tolerated. One separating unit could thus be dispensed with, which would enable a savings in capital and operating cost.

It might also be possible to achieve a degree of independence with regard to liquid flow rate in one separating unit, even if that unit is interconnected with other units, by having a compressible vapor phase in the top portion of the column comprising that unit, thereby enabling the rate adjustment by having an accumulation or reduction of the liquid inventory of the column, the desired adjustment depending on the particular portion of the component concentration distribution of which the column comprises a part at the time in question.

As previously mentioned, in addition to the embodiment of the present invention shown in FIG. 2, there are five other embodiments defined by specific correspondence between the inlets and outlets of the separating units. The other embodiment having two pumparounds is where: (a) the inlet and outlet streams of a first separating unit comprises the feed mixture inlet and zone V outlet, respectively; (b) the inlet and outlet streams of a second separating unit comprises the inlet to zone II and zone III outlet, respectively; (c) the inlet and outlet streams of a third separating unit comprises the inlet to zone I and the zone II outlet respectively; (d) the inlet and outlet streams of a fourth separating unit comprises the inlet to zone V and zone VI outlet, respectively, there being at least one additional separating unit having fluid flow comprising (e) a unit for which the inlet and outlet streams comprise the inlet and outlet, respectively, to zone IV or (f) a unit for which the inlet and outlet streams comprise the inlet and outlet, respectively, to zone VII.

A third embodiment is where: (a) the inlet and outlet streams of a first separating unit comprises the feed mixture inlet and zone II outlet, respectively: (b) the inlet and outlet streams of a second separating unit comprises the inlet to zone IV and zone VII outlet, respectively; (c) the inlet and outlet streams of a third separating unit comprises the inlet to zone II and zone VI outlet respectively; (d) the inlet and outlet streams of a fourth separating unit comprises the inlet to zone I and zone V outlet, respectively; (e) the inlet and outlet streams of a fifth separating unit comprises the inlet to zone VII and zone IV outlet, respectively; and (f) the inlet and outlet streams of a sixth separating unit comprises the inlet to zone V and zone III outlet respectively.

A fourth embodiment is where: (a) the inlet and outlet streams of a first separating unit comprises the feed mixture inlet and zone III outlet, respectively; (b) the inlet and outlet streams of a second separating unit comprises the inlet to zone IV and zone II outlet, respectively; (c) the inlet and outlet streams of a third separating unit comprises the inlet to zone II and the zone VII outlet, respectively; (d) the inlet and outlet streams of a fourth separating unit comprises the inlet to zone I and zone VI outlet, respectively; (e) the inlet and outlet streams of a fifth separating unit comprises the inlet to zone VII and zone V outlet, respectively; and (f) the inlet and outlet streams of a sixth separating unit comprises the inlet to zone V and zone IV outlet, respectively.

A fifth embodiment is where: (a) the inlet and outlet streams of a first separating unit comprises the feed mixture inlet and zone VI outlet, respectively; (b) the inlet and outlet streams of a second separating unit comprises the inlet to zone IV and zone V outlet, respectively; (c) the inlet and outlet streams of a third separating unit comprises the inlet to zone II and the zone IV outlet, respectively; (d) the inlet and outlet streams of a fourth separating unit comprises the inlet to zone I and zone III outlet, respectively; (e) the inlet and outlet streams of a fifth separating unit comprises the inlet to zone VII and zone II outlet, respectively; and (f) the inlet and outlet streams of a sixth separating unit comprises the inlet to zone V and zone VII outlet, respectively.

A sixth embodiment is where: (a) the inlet and outlet streams of a first separating unit comprises the feed mixture inlet and zone VII outlet, respectively; (b) the inlet and outlet streams of a second separating unit comprises the inlet to zone IV and zone VI outlet, respectively; (c) the inlet and outlet streams of a third separating unit comprises the inlet to zone II and the zone V outlet, respectively; (d) the inlet and outlet streams of a fourth separating unit comprises the inlet to zone I and zone IV outlet, respectively; (e) the inlet and outlet streams of a fifth separating unit comprises the inlet to zone VII and zone III outlet, respectively; and (f) the inlet and outlet streams of a sixth separating unit comprises the inlet to zone V and zone II outlet, respectively.

The following illustrative embodiments are based on the embodiment of the present invention set forth in FIG. 2 and comprise computer simulations of the separation of fructose from an aqueous solution of fructose and glucose and the separation of paraxylene from a solution of paraxylene and ethylbenzene using separating units comprising columns packed with zeolitic adsorbent having selectivity for fructose and paraxylene, respectively.

ILLUSTRATIVE EMBODIMENT I

For this illustration of the separation of fructose from an aqueous solution of fructose and glucose, the following parameters apply:

| Feed Composition: | 21 wt. % Fructose |
| --- | --- |
|  | 29 wt. % Glucose |
|  | 50 wt. % Water |
| Desorbent: | 100% Water |
| FLOW RATES: |  |
| Feed/Extract | 1.25 cc/min |
| Desorbent/Raffinate | 1.31 cc/min |
| Recycle I | 1.07 cc/min |
| Recycle II | 1.13 cc/min |
| Adsorbent Volume: | 600 cc |
| Cycle Time: | 60 minutes |

The cycle time is the time for a given column or separating unit to complete one full cycle through all the zones. A cycle is broken up into six steps of equal duration, in this case, therefore, ten minutes per step, the shifting of the various inlet and outlet streams occurring once at the end of each step.

The adsorbent volume is the total for all six separating units (100 cc each).

Recycle I and Recycle II are the pumparound flow rates of separating units 3 and 6, respectively, as shown in FIG. 2.

The selectivities of fructose with respect to glucose and water with respect to glucose are presumed to be 5.8 and 5.4, respectively.

Plug flow of liquids through the columns is not assumed, i.e. there is presumed to be a degree of axial mixing.

Figure 3:
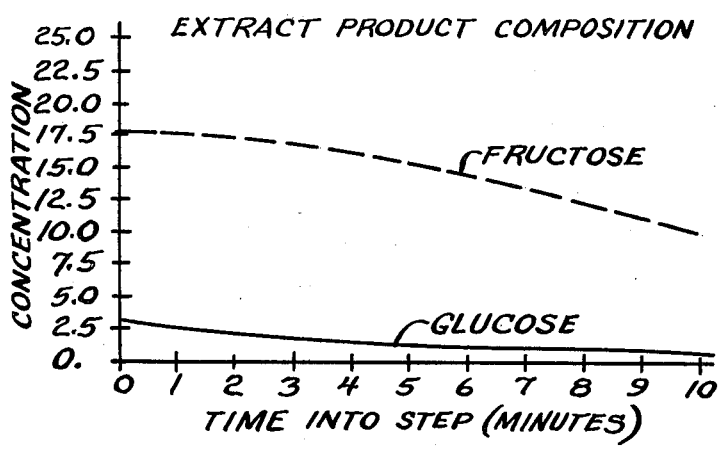
FIGS. 3 through 18 comprise graphical presentations of data obtained in computer simulations of the process of the present invention and are discussed hereinafter in greater detail in Illustrative Embodiments I and II.
Figure 4:
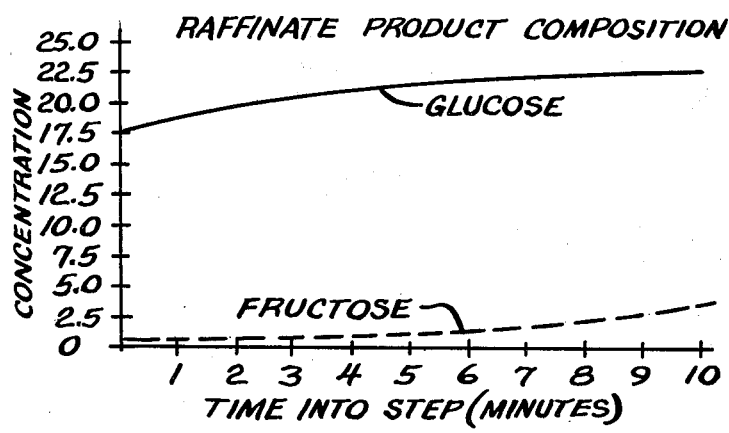
Figure 5:
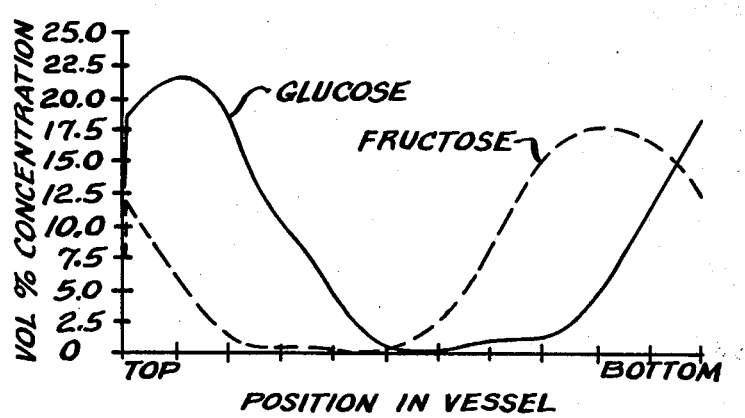
Figure 6:
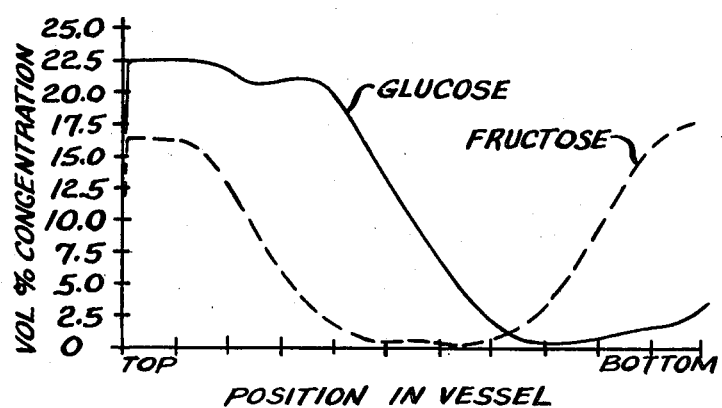
Figure 7:
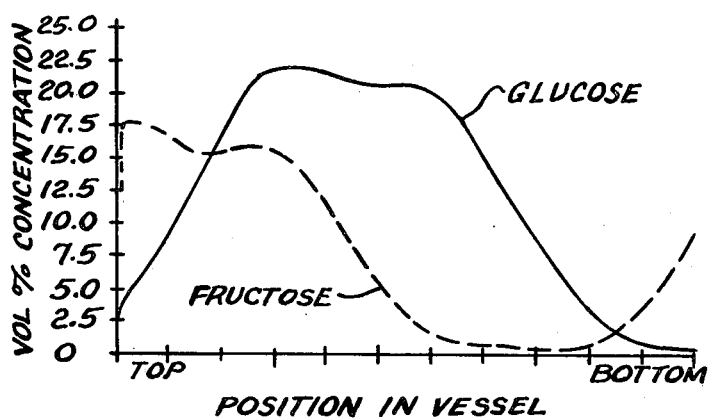
Figure 8:
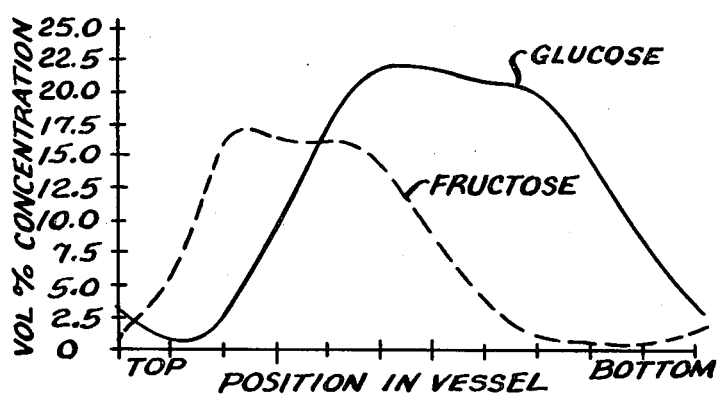
Figure 9:
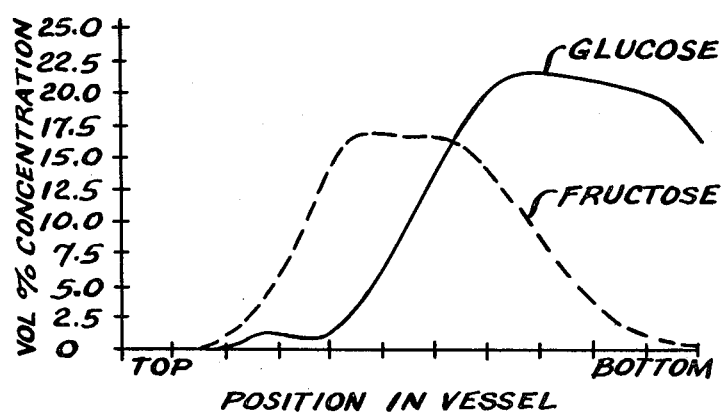
Figure 10:
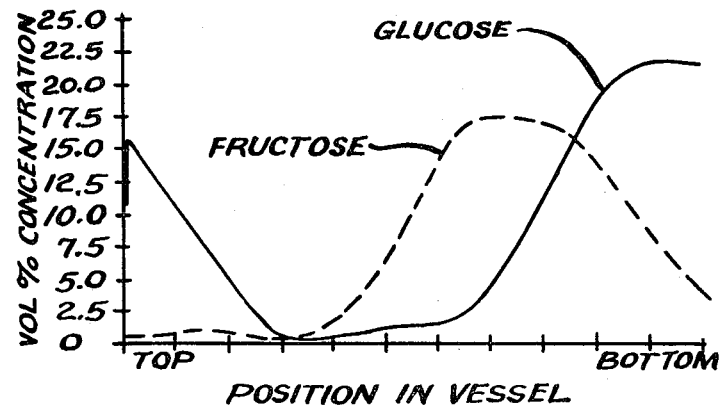

The computed plots of the compositions of the extract and raffinate output streams over the duration of one step are shown in FIGS. 3 and 4, respectively. It should be noted that the solids concentrations indicated are about 25% higher than what might be expected in the corresponding prior art simulated moving bed process. Furthermore, unlike in the prior art process it would be possible for the solids content in the feed to be greater than the indicated 50 wt.% because the lower flow rates through the beds in the process of the present invention result in a lower and more tenable pressure drop for a given liquid viscosity.

Other computed plots are shown in FIGS. 5 through 10 and comprise the fructose and glucose void liquid composition profiles from the top to the bottom of separating units 1 through 6, respectively. These profiles are as occur at the end of each step. For example, FIG. 9 corresponds to separating unit (vessel) 5 and shows at the bottom of the vessel at the instant in question a composition of almost pure glucose on a dry basis which, of course, is as desired since the vessel 5 bottom effluent is the raffinate output stream.

The computed average extract purity on a desorbent free basis is 91.4% and extract recovery via the extract output stream is 91.5%.

ILLUSTRATIVE EMBODIMENT II

For this illustration of the separation of paraxylene from a solution of paraxylene and ethylbenzene the following parameters apply:

| Feed Composition: | 25 wt. % Paraxylene |
| | 75 wt. % Ethylbenzene |
| Desorbent: | 100% Paradiethylbenzene |
| FLOW RATES: | |
| Feed/Extract | 1.51 cc/min |
| Desorbent/Raffinate | 2.20 cc/min |
| Recycle I | 2.75 cc/min |
| Recycle II | 2.20 cc/min |
| Adsorbent Volume: | 900 cc |
| Cycle Time: | 60 minutes |

The selectivities of paraxylene with respect to ethylbenzene and paradiethylbenzene with respect to ethylbenzene are 2.0 and 1.5, respectively.

Plug flow without axial mixing is assumed.

Definitions and explanations given to various terms in ILLUSTRATIVE EMBODIMENT I apply equally to this embodiment.

Figure 11:
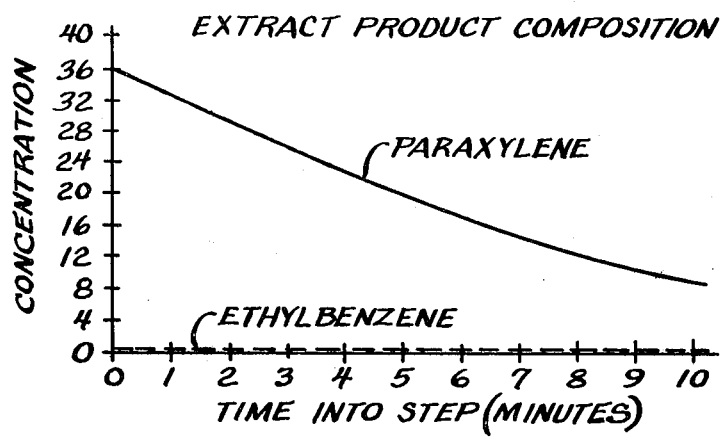
Figure 12:
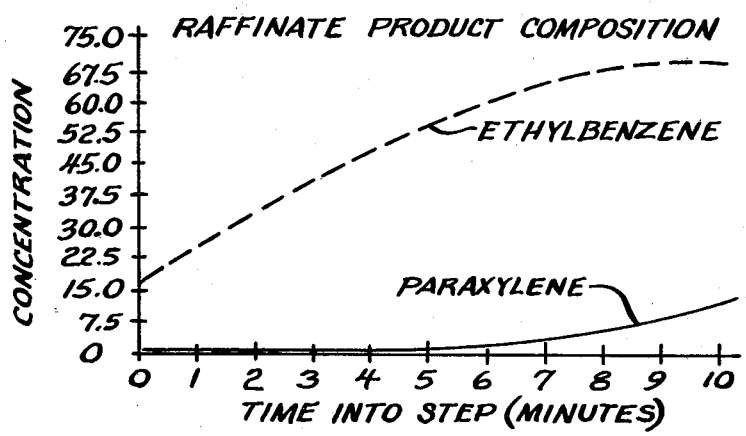
Figure 13:
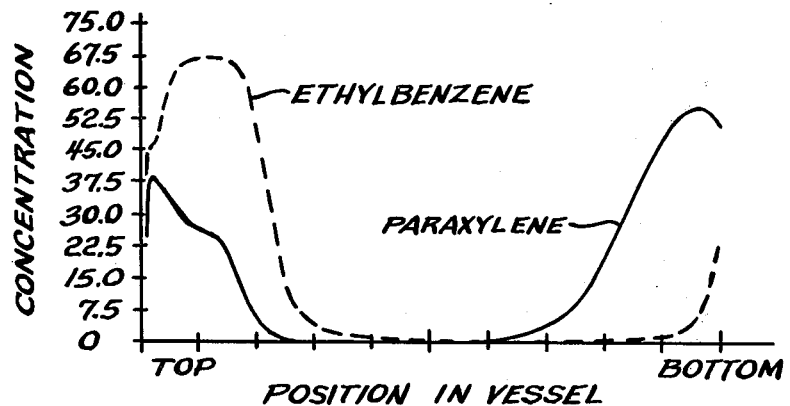
Figure 14:
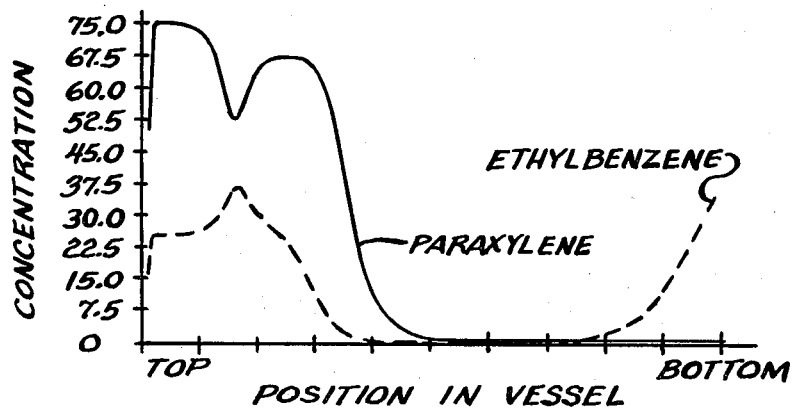
Figure 15:
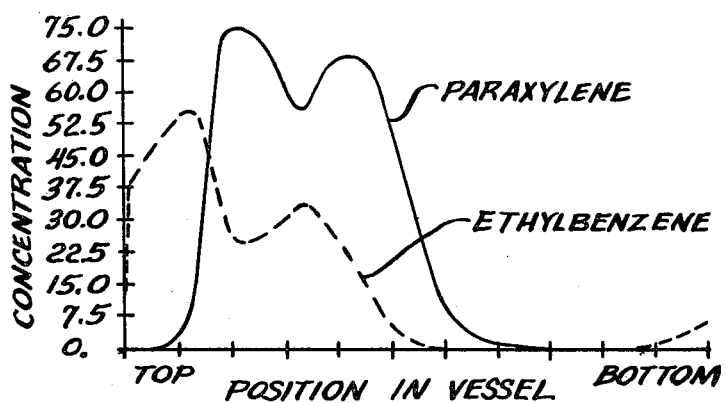
Figure 16:
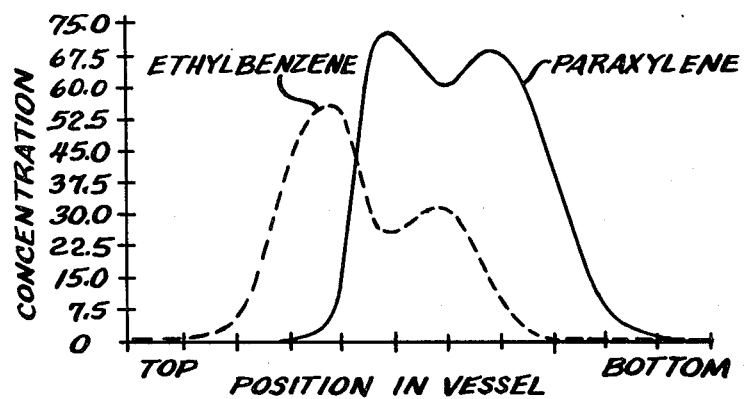
Figure 17:
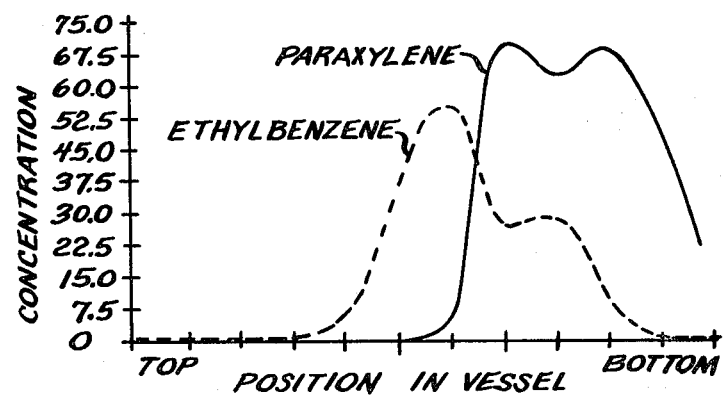
Figure 18:
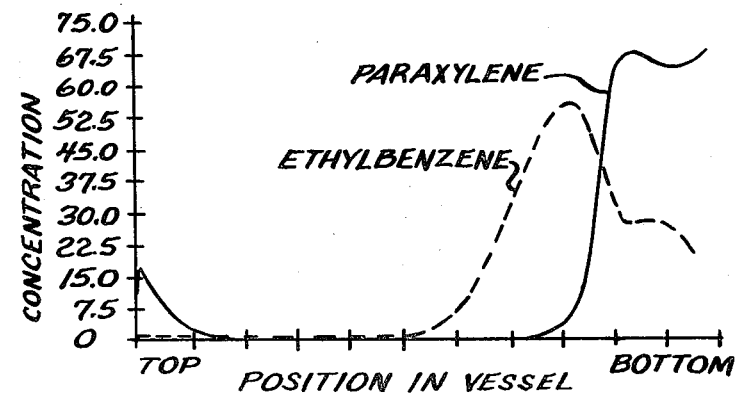

The computed plots of the compositions of the extract and raffinate output streams over the duration of one step are shown in FIGS. 11 and 12, respectively.

Other computed plots are shown in FIGS. 13 through 18 and comprise the paraxylene and ethylbenzene void liquid composition profiles from the top to the bottom of separating units 1 through 6, respectively. These profiles are as occur at the end of each step.

The computed average extract purity on a desorbent free basis is 99.8% and extract recovery via the extract output stream is 82.9%.

I claim:

1. A process for separating an extract component from a raffinate component contained in a feed mixture comprising the steps of:
    (a) maintaining a unidirectional fluid flow system through a series of separating units in which said components have differential rates of travel due to selective retardation or acceleration of each of said components in each of said units, each of said units having a fluid inlet and a fluid outlet;
    (b) passing said feed mixture into one of said fluid inlets and a displacement fluid into another of said fluid inlets, said displacement fluid being capable of displacing said components from said separating units;
    (c) establishing within a system comprising said fluid flow system a component concentration distribution, zones of which comprise, sequentially, the highest purity displacement fluid (zone I), extract component diluted with displacement fluid (zone II), concentrated extract component (zone III), extract and raffinate component mixture with the extract component being the major component (zone IV), extract and raffinate component mixture with the raffinate component being the major component (zone V), concentrated raffinate component (zone VI), and displacement fluid diluted with raffinate component (zone VII), each of said zones II, IV, V and VII having associated with it one of said fluid inlets and one of said fluid outlets, zone I having the fluid inlet for displacement fluid associated with it and each of zones III and VI having associated with it a fluid outlet, said feed mixture being passed through a fluid inlet the locus of which is at least proximate to the point on said component concentration of distribution where the relative proportions of the extract and raffinate components are the same as that occurring in the feed mixture;
    (d) withdrawing an extract stream comprising the entire flow from the fluid outlet of zone III, and withdrawing a raffinate stream comprising the entire flow from the fluid outlet of zone VI;
    (e) passing the entire stream from each of the fluid outlets of said zones II, IV, V and VII to a corresponding fluid inlet, the locuses of each said outlet and corresponding inlet being within the same zone of said component concentration distribution; and
    (f) periodically simultaneously effecting the following shifting of said inlets and outlets: the feed mixture fluid inlet to what prior to the shift was the inlet of zone V, the inlet of zone V to what had been the inlet of zone VII, the inlet of zone VII to what had been the inlet of zone I, the inlet of zone I to what had been the inlet of zone II, the inlet of zone II to what had been the inlet of zone IV, the inlet of zone IV to what had been the feed mixture inlet, the outlet of zone II to what had been the outlet of zone III, the outlet of zone III to what had been the outlet of zone IV, the outlet of zone IV to what had been the outlet of zone V, the outlet of zone V to what had been the outlet of zone VI, and the outlet of zone VI to what had been the outlet of zone VII, and the outlet of zone VII to what had been the outlet of zone II, said shifting being effected prior to the progression through said units of said component concentration distribution to the extent that the composition of the inlet or outlet streams to or from any zone becomes inconsistent with the desired composition of that zone.

2. The process of claim 1 wherein the flow rates of the fluid streams to said fluid inlets and from said fluid outlets are adjusted to provide the desired transition compositions of each inlet and outlet stream at the start and end of each flow period between said shifting.

3. The process of claim 1 wherein said separating units comprise columns at least partially packed with adsorbent having adsorptive selectivity for said extract component as compared to said raffinate component, there being at least one of said columns for each said separating unit, said displacement fluid comprising a desorbent capable of effecting desorption of said extract component from said adsorbent, said feed mixture being contacted with said adsorbent at adsorption conditions and said desorbent being contacted with said adsorbent at desorption conditions.

4. The process of claim 3 wherein said fluid flow system is in liquid phase and said adsorption and desorption conditions comprise temperature and pressures which effect said liquid phase.

5. The process of claim 4 wherein a top portion of each column comprises a compressible vapor phase, thereby enabling an accumulation or reduction of the liquid inventory of said column as desired depending on the particular portion of said component concentration distribution of which said column comprises a part at the time in question.

6. The process of claim 1 wherein the following correspondence exists between the inlets and outlets of said units: (a) the inlet and outlet streams of a first separating unit comprises the feed mixture inlet and zone II outlet, respectively; (b) the inlet and outlet streams of a second separating unit comprises the inlet to zone IV and zone VII outlet, respectively; (c) the inlet and outlet streams of a third separating unit comprises the inlet to zone II and zone VI outlet respectively; (d) the inlet and outlet streams of a fourth separating unit comprises the inlet to zone I and zone V outlet, respectively; (e) the inlet and outlet streams of a fifth separating unit comprises the inlet to zone VII and zone IV outlet, respectively; and (f) the inlet and outlet streams of a sixth separating unit comprises the inlet to zone V and zone III outlet, respectively.

7. The process of claim 1 wherein the following correspondence exists between the inlets and outlets of said units: (a) the inlet and outlet streams of a first separating unit comprises the feed mixture inlet and zone III outlet, respectively; (b) the inlet and outlet streams of a second separating unit comprises the inlet to zone IV and zone II outlet, respectively; (c) the inlet and outlet streams of a third separating unit comprises the inlet to zone II and the zone VII outlet respectively; (d) the inlet and outlet streams of a fourth separating unit comprises the inlet to zone I and zone VI outlet, respectively; (e) the inlet and outlet streams of a fifth separating unit comprises the inlet to zone VII and zone V outlet, respectively; and (f) the inlet and outlet streams of a sixth separating unit comprises the inlet to zone V and zone IV outlet, respectively.

8. The process of claim 1 wherein the following correspondence exists between the inlets and outlets of said units: (a) the inlet and outlet streams of a first separating unit comprises the feed mixture inlet and zone IV outlet, respectively; (b) the inlet and outlet streams of a second separating unit comprises the inlet to zone IV and zone III outlet, respectively; (c) the inlet and outlet streams of a third separating unit comprises the inlet to zone I and the zone VII outlet respectively; (d) the inlet and outlet streams of a fourth separating unit comprises the inlet to zone VII and zone VI outlet, respectively, there being at least one additional separating unit having fluid flow comprising (e) a unit for which the inlet and outlet streams comprise the inlet and outlet, respectively, to zone II; or (f) a unit for which the inlet and outlet streams comprise the inlet and outlet, respectively, to zone V.

9. The process of claim 1 wherein the following correspondence exists between the inlets and outlets of said units: (a) the inlet and outlet streams of a first separating unit comprises the feed mixture inlet and zone V outlet, respectively; (b) the inlet and outlet streams of a second separating unit comprises the inlet to zone II and zone III outlet, respectively; (c) the inlet and outlet streams of a third separating unit comprises the inlet to zone I and the zone II outlet respectively; (d) the inlet and outlet streams of a fourth separating unit comprises the inlet to zone V and zone VI outlet, respectively, there being at least one additional separating unit having fluid flow comprising (e) a unit for which the inlet and outlet streams comprise the inlet and outlet, respectively, to zone IV or (f) a unit for which the inlet and outlet streams comprise the inlet and outlet, respectively, to zone VII.

10. The process of claim 1 wherein the following correspondence exists between the inlets and outlets of said units: (a) the inlet and outlet streams of a first separating unit comprises the feed mixture inlet and zone VI outlet, respectively; (b) the inlet and outlet streams of a second separating unit comprises the inlet to zone IV and zone V outlet, respectively; (c) the inlet and outlet streams of a third separating unit comprises the inlet to zone II and the zone IV outlet respectively; (d) the inlet and outlet streams of a fourth separating unit comprises the inlet to zone I and zone III outlet, respectively; (e) the inlet and outlet streams of a fifth separating unit comprises the inlet to zone VII and zone II outlet, respectively; and (f) the inlet and outlet streams of a sixth separating unit comprises the inlet to zone V and zone VII outlet, respectively.

11. The process of claim 1 wherein the following correspondence exists between the inlets and outlets of said units: (a) the inlet and outlet streams of a first separating unit comprises the feed mixture inlet and zone VII outlet, respectively; (b) the inlet and outlet streams of a second separating unit comprises the inlet to zone IV and zone VI outlet, respectively; (c) the inlet and outlet streams of a third separating unit comprises the inlet to zone II and the zone V outlet respectively; (d) the inlet and outlet streams of a fourth separating unit comprises the inlet to zone I and zone IV outlet, respectively; (e) the inlet and outlet streams of a fifth separating unit comprises the inlet to zone VII and zone III outlet, respectively; and (f) the inlet and outlet streams of a sixth separating unit comprises the inlet to zone V and zone II outlet, respectively.

* * * * *